(12) United States Patent
Kirschman (10) Patent No.: US 8,979,934 B2
(45) Date of Patent: Mar. 17, 2015

(54) COMPOSITE ORTHOPEDIC IMPLANT HAVING A LOW FRICTION MATERIAL SUBSTRATE WITH PRIMARY FRICTIONAL FEATURES AND SECONDARY FRICTIONAL FEATURES

(71) Applicant: David Louis Kirschman, Dayton, OH (US)

(72) Inventor: David Louis Kirschman, Dayton, OH (US)

(73) Assignee: X-spine Systems, Inc., Miamisburg, OH (US)

( * ) Notice: Subject to any disclaimer, the term of this patent is extended or adjusted under 35 U.S.C. 154(b) by 0 days.

(21) Appl. No.: 14/154,577

(22) Filed: Jan. 14, 2014

(65) Prior Publication Data

US 2014/0128980 A1    May 8, 2014

Related U.S. Application Data

(63) Continuation of application No. 13/184,856, filed on Jul. 18, 2011, now abandoned.

(60) Provisional application No. 61/365,912, filed on Jul. 20, 2010.

(51) Int. Cl.
*A61F 2/44* (2006.01)
*A61F 2/30* (2006.01)
*A61F 2/46* (2006.01)

(52) U.S. Cl.
CPC ............. *A61F 2/447* (2013.01); *A61F 2/30767* (2013.01); *A61F 2/4611* (2013.01); *A61F 2002/30014* (2013.01); *A61F 2002/30024* (2013.01); *A61F 2002/30321* (2013.01); *A61F 2002/30448* (2013.01); *A61F 2002/30451* (2013.01);

(Continued)

(58) Field of Classification Search
USPC ........................................... 623/17.11–17.16
See application file for complete search history.

(56) References Cited

U.S. PATENT DOCUMENTS 4,194,384 A * 3/1980 Fujie et al. ...................... 72/325
4,713,076 A * 12/1987 Draenert ...................... 623/23.6

(Continued)

FOREIGN PATENT DOCUMENTS

| EP | 1103237 | 5/2001 |
| WO | 2004017857 | 3/2004 |
| WO | 2006119092 | 11/2006 |

OTHER PUBLICATIONS

Materials Data Book. Cambridge University Engineering Department, n. d. Web. Feb. 27, 2013. <http://www-mdp.eng.cam.ac.uk/web/library/enginfo/cueddatabooks/materials.pdf>.

*Primary Examiner* — Todd Manahan
*Assistant Examiner* — Eric S Gibson
(74) *Attorney, Agent, or Firm* — Jacox, Meckstroth & Jenkins (57) ABSTRACT

An orthopedic implant comprising a substrate material adapted to provide the orthopedic implant. The implant has a primary friction area located on or integral with the substrate material. The primary friction area defining an engagement surface having a primary frictional feature. A secondary friction area is located on or integral with the engagement surface and defining a second frictional feature. The primary friction area and the secondary friction area defining a friction interface zone between the orthopedic implant and at least one bone. The secondary friction area increases a friction of the engagement surface and modulus of elasticity to enhance the frictional engagement between the engagement surface and the at least one bone.

44 Claims, 10 Drawing Sheets

(52) U.S. Cl.
CPC .......... *A61F2002/30769* (2013.01); *A61F 2002/30789* (2013.01); *A61F 2002/30841* (2013.01); *A61F 2002/30892* (2013.01); *A61F 2002/30904* (2013.01); *A61F 2002/30906* (2013.01); *A61F 2002/3092* (2013.01); *A61F 2002/30924* (2013.01); *A61F 2002/30929* (2013.01); *A61F 2002/3098* (2013.01); *A61F 2250/0021* (2013.01); *A61F 2310/00407* (2013.01); *A61F 2310/00413* (2013.01)
USPC ............................. 623/17.16; 623/17.11

(56) References Cited

U.S. PATENT DOCUMENTS

| | | | |
|---|---|---|---|
| 4,714,469 A | 12/1987 | Kenna | |
| 4,828,563 A * | 5/1989 | Muller-Lierheim | 623/23.63 |
| 4,834,757 A | 5/1989 | Brantigan | |
| 4,863,477 A | 9/1989 | Monson | |
| 4,865,603 A * | 9/1989 | Noiles | 623/23.5 |
| 5,071,437 A | 12/1991 | Steffee | |
| 5,306,307 A * | 4/1994 | Senter et al. | 623/17.16 |
| 5,306,308 A * | 4/1994 | Gross et al. | 623/17.16 |
| 5,405,389 A | 4/1995 | Conta et al. | |
| 5,425,772 A | 6/1995 | Brantigan | |
| 5,443,514 A | 8/1995 | Steffee | |
| 5,505,736 A | 4/1996 | Reimels et al. | |
| 5,507,815 A * | 4/1996 | Wagner et al. | 623/23.5 |
| 5,522,899 A | 6/1996 | Michelson | |
| 5,534,030 A | 7/1996 | Navarro et al. | |
| 5,554,191 A | 9/1996 | Lahille et al. | |
| 5,607,607 A * | 3/1997 | Naiman et al. | 219/121.68 |
| 5,683,463 A | 11/1997 | Godefroy et al. | |
| 5,702,450 A | 12/1997 | Bisserie | |
| 5,747,106 A * | 5/1998 | Matsunaga | 427/195 |
| 5,824,094 A | 10/1998 | Serhan et al. | |
| 5,865,845 A | 2/1999 | Thalgott | |
| 5,876,457 A * | 3/1999 | Picha et al. | 623/17.11 |
| 5,980,522 A | 11/1999 | Koros et al. | |
| 6,008,432 A * | 12/1999 | Taylor | 623/23.3 |
| 6,139,579 A | 10/2000 | Steffee et al. | |
| 6,143,033 A * | 11/2000 | Paul et al. | 623/17.11 |
| 6,176,882 B1 | 1/2001 | Biedermann et al. | |
| 6,241,771 B1 | 6/2001 | Gresser et al. | |
| 6,258,125 B1 | 7/2001 | Paul et al. | |
| 6,346,122 B1 * | 2/2002 | Picha et al. | 623/17.11 |
| 6,432,107 B1 | 8/2002 | Ferree | |
| 6,454,806 B1 | 9/2002 | Cohen et al. | |
| 6,454,807 B1 | 9/2002 | Jackson | |
| 6,458,159 B1 * | 10/2002 | Thalgott | 623/17.11 |
| 6,491,723 B1 * | 12/2002 | Beaty | 623/11.11 |
| 6,520,993 B2 * | 2/2003 | James et al. | 623/17.16 |
| 6,558,424 B2 * | 5/2003 | Thalgott | 623/17.16 |
| 6,562,074 B2 | 5/2003 | Gerbec et al. | |
| 6,569,201 B2 * | 5/2003 | Moumene et al. | 623/17.11 |
| 6,572,654 B1 * | 6/2003 | Santilli | 623/17.16 |
| 6,582,432 B1 | 6/2003 | Michelson | |
| 6,592,624 B1 | 7/2003 | Fraser et al. | |
| 6,620,196 B1 * | 9/2003 | Trieu | 623/17.16 |
| 6,669,732 B2 | 12/2003 | Serhan et al. | |
| 6,719,794 B2 | 4/2004 | Gerber et al. | |
| 6,852,129 B2 | 2/2005 | Gerbec et al. | |
| 6,863,673 B2 | 3/2005 | Gerbec et al. | |
| 6,921,264 B2 | 7/2005 | Mayer et al. | |
| 7,008,226 B2 | 3/2006 | Mayer et al. | |
| 7,217,293 B2 * | 5/2007 | Branch, Jr. | 623/17.16 |
| 7,226,483 B2 | 6/2007 | Gerber et al. | |
| 7,276,081 B1 * | 10/2007 | Coates et al. | 623/17.11 |
| 7,276,082 B2 * | 10/2007 | Zdeblick et al. | 623/17.15 |
| 7,320,707 B2 * | 1/2008 | Zucherman et al. | 623/17.14 |
| 7,556,648 B2 * | 7/2009 | Picha et al. | 623/17.11 |
| 7,621,956 B2 | 11/2009 | Paul et al. | |
| 7,637,950 B2 * | 12/2009 | Baccelli et al. | 623/17.11 |
| 7,637,953 B2 | 12/2009 | Branch et al. | |
| 7,641,666 B2 | 1/2010 | Paul et al. | |
| 7,655,046 B2 | 2/2010 | Dryer et al. | |
| 7,678,148 B2 | 3/2010 | Peterman | |
| 7,704,280 B2 * | 4/2010 | Lechmann et al. | 623/17.15 |
| 7,723,395 B2 * | 5/2010 | Ringeisen et al. | 521/50 |
| 7,857,987 B2 * | 12/2010 | Beaty | 216/109 |
| 7,892,262 B2 | 2/2011 | Rhoda et al. | |
| 7,938,860 B2 * | 5/2011 | Trieu | 623/17.16 |
| 7,988,733 B2 * | 8/2011 | Shimp et al. | 623/17.11 |
| 7,988,734 B2 * | 8/2011 | Peterman et al. | 623/17.11 |
| 8,002,837 B2 * | 8/2011 | Stream et al. | 623/17.16 |
| 8,043,377 B2 * | 10/2011 | Guyer et al. | 623/17.11 |
| 8,097,036 B2 | 1/2012 | Cordaro et al. | |
| 8,182,532 B2 * | 5/2012 | Anderson et al. | 623/17.11 |
| 8,252,059 B2 * | 8/2012 | Overes et al. | 623/17.15 |
| 8,262,737 B2 * | 9/2012 | Bagga et al. | 623/17.16 |
| 8,268,002 B2 * | 9/2012 | Blackwell et al. | 623/17.16 |
| 8,343,219 B2 * | 1/2013 | Allain et al. | 623/17.11 |
| 8,470,038 B2 * | 6/2013 | Bianchi et al. | 623/13.14 |
| 8,585,764 B2 * | 11/2013 | Copf, Jr. | 623/17.16 |
| 8,663,293 B2 * | 3/2014 | Assell et al. | 606/279 |
| 2001/0016773 A1 * | 8/2001 | Serhan et al. | 623/17.15 |
| 2001/0039454 A1 * | 11/2001 | Ricci et al. | 623/23.5 |
| 2002/0022888 A1 | 2/2002 | Serhan et al. | |
| 2002/0133232 A1 * | 9/2002 | Ricci et al. | 623/23.5 |
| 2003/0100951 A1 * | 5/2003 | Serhan et al. | 623/17.16 |
| 2004/0038180 A1 | 2/2004 | Mayer et al. | |
| 2004/0053196 A1 | 3/2004 | Mayer et al. | |
| 2004/0181286 A1 * | 9/2004 | Michelson | 623/23.5 |
| 2005/0038511 A1 * | 2/2005 | Martz et al. | 623/17.11 |
| 2005/0043800 A1 | 2/2005 | Paul et al. | |
| 2005/0119758 A1 * | 6/2005 | Alexander et al. | 623/23.5 |
| 2006/0036325 A1 | 2/2006 | Paul et al. | |
| 2006/0069440 A1 | 3/2006 | Zucherman et al. | |
| 2006/0129240 A1 * | 6/2006 | Lessar et al. | 623/17.14 |
| 2006/0149376 A1 | 7/2006 | Shimp et al. | |
| 2006/0217807 A1 * | 9/2006 | Peterman et al. | 623/17.11 |
| 2007/0010826 A1 | 1/2007 | Rhoda et al. | |
| 2007/0027544 A1 * | 2/2007 | McCord et al. | 623/17.11 |
| 2007/0276499 A1 | 11/2007 | Paul et al. | |
| 2008/0154377 A1 | 6/2008 | Voellmicke | 623/17.16 |
| 2008/0154378 A1 | 6/2008 | Pelo | 623/17.16 |
| 2008/0183293 A1 * | 7/2008 | Parry et al. | 623/17.11 |
| 2009/0054986 A1 | 2/2009 | Cordaro et al. | |
| 2009/0082849 A1 * | 3/2009 | Link | 623/1.15 |
| 2009/0234458 A1 * | 9/2009 | de Villiers et al. | 623/17.16 |
| 2009/0276051 A1 * | 11/2009 | Arramon et al. | 623/17.16 |
| 2010/0042218 A1 * | 2/2010 | Nebosky et al. | 623/17.12 |
| 2010/0131074 A1 * | 5/2010 | Shikinami | 623/23.5 |
| 2010/0262244 A1 * | 10/2010 | Savage-Erickson et al. | 623/17.16 |
| 2010/0312347 A1 * | 12/2010 | Arramon et al. | 623/17.16 |
| 2011/0022181 A1 * | 1/2011 | Kasahara et al. | 623/23.5 |
| 2012/0022653 A1 * | 1/2012 | Kirschman | 623/17.16 |
| 2012/0101579 A1 * | 4/2012 | de Villiers et al. | 623/17.16 |
| 2012/0109302 A1 * | 5/2012 | Miller et al. | 623/17.11 |
| 2012/0265306 A1 * | 10/2012 | Trieu | 623/17.16 |
| 2012/0316650 A1 * | 12/2012 | Ullrich et al. | 623/17.16 |
| 2013/0006363 A1 * | 1/2013 | Ullrich et al. | 623/17.16 |
| 2013/0018471 A1 * | 1/2013 | Davenport et al. | 623/17.16 |
| 2013/0116793 A1 * | 5/2013 | Kloss | 623/17.16 |
| 2013/0197645 A1 * | 8/2013 | Assell et al. | 623/17.16 |

\* cited by examiner

COMPOSITE ORTHOPEDIC IMPLANT HAVING A LOW FRICTION MATERIAL SUBSTRATE WITH PRIMARY FRICTIONAL FEATURES AND SECONDARY FRICTIONAL FEATURES

CROSS-REFERENCE TO RELATED APPLICATIONS

The present application is a continuation of U.S. application Ser. No. 13/184,856 filed Jul. 18, 2011, which claims priority to provisional U.S. Application Ser. No. 61/365,912 filed Jul. 20, 2010, to which Applicant claims the benefit of the earlier filing date. These applications are incorporated herein by reference and made a part hereof.

BACKGROUND OF THE INVENTION

1. Field of the Invention

This invention relates to a composite orthopedic implant having a low friction material substrate with primary frictional features and secondary frictional features.

2. Description of the Related Art

The placement of spinal implants between vertebrae is a common surgical procedure. A number of such spinal implants, which are generally hollow and box-shaped or cylindrical, have been developed. One risk of such procedures is the post-operative expulsion or dislocation of the implanted device. There is a need to increase the frictional forces between the device and the bone surface.

The most advantageous material for the manufacture of intervertebral spinal implants is thermoplastic polymer, of which the most commonly used is polyetheretherketone (PEEK). This material has proven biocompatibility with human tissue and is biomechanically strong enough to withstand long-term cyclical loading as occurs within the spine. This type of material has a modulus of elasticity similar to bone, reducing the probability of bone subsidence which can occur with harder metallic implants. A significant problem, however, with the use of such polymeric spinal implants is inherent low levels of bone-device surface interaction. Machined or molded polymeric materials tend to have relatively high levels of lubricity, elasticity, and smoothness which conspire to reduce friction at the bone-device interface. This can result in undesirably low frictional forces between bone and the implanted device. Several parties have attempted to address this issue by adding large frictional features to the polymer implant. These features are typically exemplified by surface teeth of various designs. Although surface teeth increase interface friction somewhat, the underlying challenges of lubricity, smoothness and elasticity remain.

What is needed, therefore, is a polymer implant that builds upon the current state of the art.

SUMMARY OF THE INVENTION

One object of an embodiment is to provide simple frictional features that add a metallic surface material which has features of low lubricity, low elasticity and secondary frictional features. Such a design will maintain the desirable biomechanical properties of the polymeric implant itself while addressing frictional shortcomings at the bone-device interface. Physical properties of the metallic surface can be further optimized using dispersed deposition techniques onto the polymeric substrate.

A composite bone-device interface used, in its preferred embodiment, in an orthopedic implant for the support of spinal vertebrae. The interface is manufactured from, in its preferred embodiment, a combination of biocompatible materials, which comprise a bone-device interface zone. The interface zone comprises a relatively low friction polymeric substrate material and primary frictional features. The primary frictional features further comprise a high-friction surface material containing secondary frictional features.

One object of one embodiment is to provide a primary friction feature in combination with a secondary friction feature.

Another object is to provide an embodiment where the primary friction feature is integral with the body and comprises the same material as the body, such as a polymeric substrate, whereas the secondary friction feature which is integral with, applied to, deposited on or otherwise adhered to the primary friction feature is of a different substrate, such as a metal or a metal alloy.

Still another object is to provide a surgical implant having improved frictional engagement at the bone-implant engaging interfaces.

Still another object is to provide an embodiment wherein the secondary frictional features are plasma vapor depositions on the primary frictional features.

Still another embodiment is to provide an implant having a body with both primary frictional features and secondary frictional features.

Yet another object of one embodiment is to provide primary and secondary frictional features in the form of teeth or serrations that can be regular or irregular in shape, discontinuous or continuous or otherwise have different or the same shape or configuration with respect to each other.

Another object of an embodiment is to provide secondary frictional features in the form of elongated teeth that are situated on or integral with the primary frictional features, which in one embodiment are also teeth, and which are either regular and uninterrupted or irregular and interrupted.

In one aspect, one embodiment comprises an orthopedic implant comprising a substrate material adapted to provide said orthopedic implant, a primary friction area located on or integral with said substrate material, said primary friction area having a primary surface having a primary frictional feature, and a secondary friction area located on or integral with said primary surface and defining a secondary frictional feature, said primary friction area and said secondary friction area defining a friction interface zone, said secondary friction area increasing a friction of said primary surface to enhance said frictional engagement between said primary surface and at least one bone, wherein said primary surface defines a plurality of teeth or serrations, wherein said secondary frictional feature defines a plurality of teeth, points or peaks on or integral with said primary friction area.

In another aspect, another embodiment comprises an orthopedic implant comprising a body comprising a composite material, a first friction area situated between said body and bone of a patient when said orthopedic implant is implanted in said patient, said first friction area comprising a plurality of teeth or serrations, and a second friction area associated with said first friction area for directly engaging said bone, wherein said secondary frictional feature defines a plurality of teeth, points or peaks on or integral with said primary friction area, each of said first and second friction areas for improving a frictional engagement between said bone and said orthopedic implant.

In yet another aspect, another embodiment comprises a method for improving a frictional interface between an implant and bone of a patient, comprising said steps of processing a body to comprise a primary friction feature, processing said body to comprise a secondary friction feature directly on or integral with said primary friction feature.

These and other objects and advantages will be apparent from the following description, the accompanying drawings and the appended claims.

BRIEF DESCRIPTION OF THE DRAWINGS

FIG. 11 illustrates the primary friction feature and secondary friction feature in the form of teeth having different shapes, pitches, pitch thickness and the like.

DETAILED DESCRIPTION OF PREFERRED EMBODIMENTS

Referring now to FIGS. 1-5, a first embodiment of an orthopedic implant 10 is shown. The orthopedic implant 10 comprises a body 12 that is adapted to provide or define the orthopedic implant 10. In the illustration being described, the orthopedic implant 10 could be a spinal implant, such as a cage, plate or other implant wherein surfaces of the orthopedic implant 10 engage, for example, bone of a patient. In one application, the orthopedic implant 10 is situated between adjacent vertebrae (not shown) of a patient. In the illustration being described, the orthopedic implant 10 comprises the body 12 made from a substrate or composite material, such as a polymeric material. The polymeric material may be a thermoplastic material, such as polyetheretherketone (PEEK). The substrate or composite material has a low coefficient of friction with bone.

The orthopedic implant 10 defines an orthopedic cage 11 in this illustration having a plurality of walls 14a, 14b, 14c and 14d. The walls 14a and 14c have windows 18 and 20 as shown. The orthopedic implant 10 has a plurality of walls 21 that define tool apertures 22 for receiving a tool (not shown) for placement of the orthopedic implant 10, for example, between adjacent vertebrae (not shown) in the patient.

The implant 10 further has a first end 12a and a second end 12b. As best illustrated in FIGS. 2-5, note that the orthopedic implant 10 comprises a first or primary friction area, layer or feature 24 applied to, adhered to or integrally formed on each ends 12a and 12b. In the illustration, the body 12 defines a cage 11 that has four bone-engaging areas or surfaces 12a1, 12a2, 12b1 and 12b2.

In the illustration being described, the first or primary friction area, layer or feature 24 comprises or is adapted to define a first plurality of teeth or serrations 26 which are integrally formed in the surfaces 12a1, 12a2, 12b1 and 12b2 as shown. The body 12 is machined, molded, extruded, centered, cast or has a deposited substrate that is applied to the body 12 to provide or define the first or primary friction area, layer or feature 24. Although not shown, it should be appreciated that the first or primary friction area, layer or feature 24 may be separate from and non-integral with the body 12, for example, but that is secured thereto by a weld, bond adhesive or other type of fixation. In the illustration being described relative to FIGS. 1-3, the first or primary friction area, layer or feature 24 comprises the first plurality of teeth or serrations 26 that are integral with the body 12 and both are made of the same polymeric substrate, such as polyetheretherketone (PEEK). Alternatively, the body 12 could be made from a polymeric substrate while the first or primary friction area, layer or feature 24 may comprise a metallic or metallic alloy that is applied or, adhered to or otherwise affixed or secured to the body 12. After the orthopedic implant 10 is implanted into the patient, the first or primary friction area, layer or feature 24 becomes situated between the body 12 and the bone of the patient, such as the adjacent vertebra (not shown).

As mentioned earlier, the first or primary friction area, layer or feature 24 comprises the first plurality of teeth or serrations 26 that are integral with both ends 12a and 12b of the body 12, and each of the areas or surfaces 12a1, 12a2, 12b1 and 12b2 have the first plurality of teeth or serrations 26. For ease of illustration, portions of the first plurality of teeth or serrations 26 on the surface 12a2 are shown fragmentarily and enlarged in FIGS. 2 and 3, but it should be understood that the first plurality of teeth or serrations 26 of the first or primary friction area, layer or feature 24 on the other portions of surface 12a2 and on the other surfaces 12a1, 12b1 and 12b2 are substantially the same in this embodiment.

Figure 1:
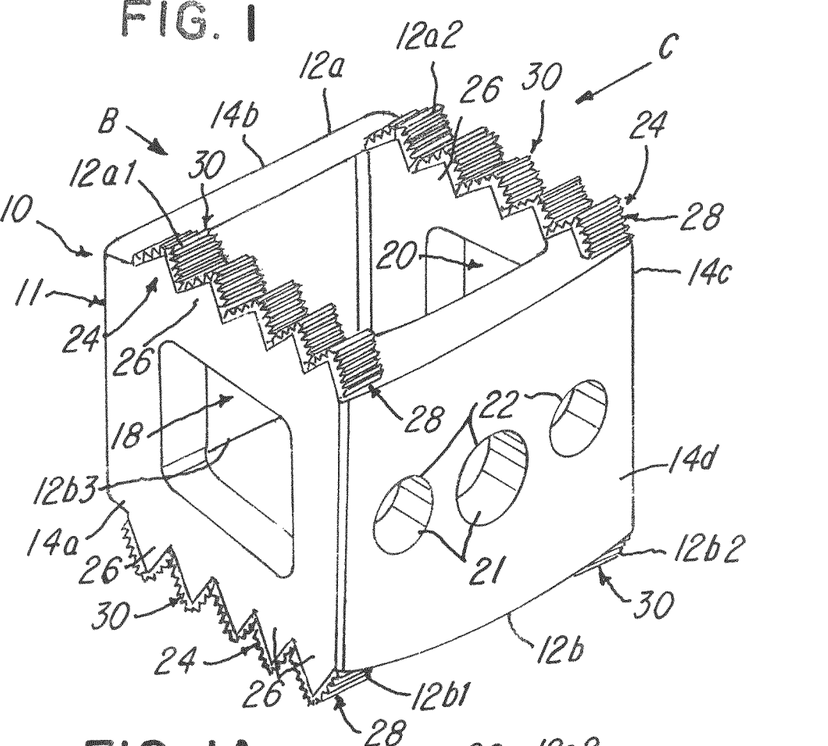
FIG. 1 is a perspective view of one embodiment.
Figure 1A:
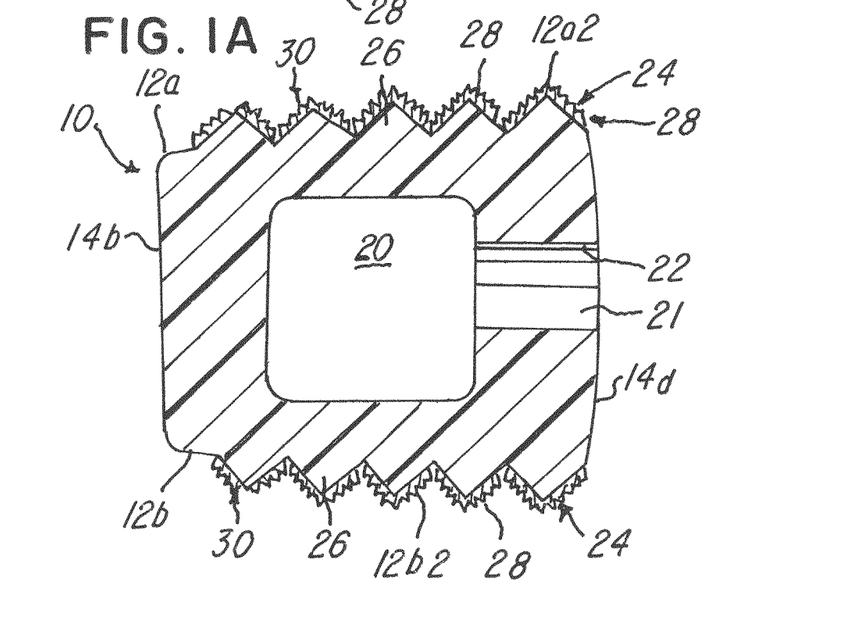
FIG. 1A is sectional view taken along the line 1A-1A in FIG. 1.

The orthopedic implant 10 further comprises a second or secondary friction area, layer or feature 28 associated with the first or primary friction area, layer or feature 24. In the illustration being described, the second or secondary friction area, layer or feature 28 is applied to, deposited on, adhered to, bonded, located on or integral with the first or primary friction area, layer or feature 24 as shown. In the illustration being shown in FIGS. 1-3, the first or primary friction area, layer or feature 24 and the second or secondary friction area, layer or feature 28 cooperate to define a plurality of friction interface zones 30 (FIGS. 1-1A).

The second or secondary friction area, layer or feature 28 is applied to, deposited on, adhered to, located on or adhered to teeth surfaces, such as surfaces 26a and 26b (FIG. 2) of each of the first plurality of teeth or serrations 26 on the surfaces 12a1, 12a2, 12b1 and 12b2 where the orthopedic implant 10 engages bone and increases a friction between each of the first plurality of teeth or serrations 26 and the bone of the patient.

It has been found that the enhanced frictional engagement facilitates maintaining the position of the orthopedic implant 10 in the patient. For example, it is desirable that the cage 11 illustrated in FIGS. 1 to 5 not move after it is implanted in the patient, and the second or secondary friction area, layer or feature 28 enhances the frictional engagement between the first or primary friction area, layer or feature 24 and the bone of the patient to prevent or minimize such movement.

The first or primary friction area, layer or feature 24 comprises a first or primary friction feature in the form of the first plurality of teeth or serrations 26, and the second or secondary friction area, layer or feature 28 comprises a second or secondary friction feature that enhances the orthopedic implant's 10 friction interface zone 30. In the embodiment of FIGS. 1-3, 6A-6B, 7, 8A-8B, 9A-9B, 11 and 12A-12B, the second or secondary friction area, layer or feature 28 comprises a second plurality of teeth or serrations 32 integral with, deposited on, adhered to or otherwise applied to one or more of the first plurality of teeth or serrations 26 as shown. The body 12, the first or primary friction area, layer or feature 24 and the second or secondary friction area, layer or feature 28 is manufactured from, in its preferred embodiment, a combination of bio-compatible materials, including but not limited to, at the friction interface zone 30.

In the illustration being described, the second or secondary friction area, layer or feature 28 may comprise a microscopically and/or macroscopically rough or porous surface, which enhances the frictional engagement between the first or primary friction area, layer or feature 24 and the bone of the patient. The rough surface may be provided by, for example, sand blasting, coating, plasma spraying, vapor deposition, adhering a frictional layer, peening or even laser shock peening.

The secondary friction features may comprise a machined, molded, extruded, sintered or deposited surface material. In the illustration of FIGS. 4-5, 10A and 10B, the deposited surface material may comprise a coating or deposition that is sprayed onto, melted to or otherwise applied or adhered to the primary surface 26a of the first or primary friction area, layer or feature 24. In the embodiment shown in FIGS. 4, 5, 7 and 10A-10B, the coating or deposition is a plasma vapor deposition applied using a conventional plasma vapor deposition process. Thus, it should be understood that the second or secondary friction area, layer or feature 28 may be integral with, welded to, machined into, adhered to, deposited on or otherwise affixed, processed or applied to the first or primary friction area, layer or feature 24.

In the illustrations being described, the body 12, the first or primary friction area, layer or feature 24 and the second or secondary friction area, layer or feature 28 may be made from the same bio-compatible material or one or more of them can comprise or be made from different bio-compatible materials. In one embodiment, each of the body 12 and the first or primary friction area, layer or feature 24 are made of a bio-compatible polymeric substrate, such as polyetheretherketone (PEEK), while the second or secondary friction area, layer or feature 28 is comprised of a metal or metallic alloy. In the embodiments of FIGS. 1-5, the body 12 and the first or primary friction area, layer or feature 24 are integral and monolithically formed and are made from the same PEEK material, while the second or secondary friction area, layer or feature 28 is a metallic material, metal, or metallic alloy, such as titanium, cobalt or associated alloys. It should be understood that the body 12, first or primary friction area, layer or feature 24 and the second or secondary friction area, layer or feature 28 could be the same material, such as a polymer, a metal or metal alloy or different materials.

The body 12 and the first or primary friction area, layer or feature 24 comprise the polymeric substrate have a relatively low modulus of elasticity and/or a modulus of elasticity equivalent to bone while the second or secondary friction area, layer or feature 28 has a higher modulus elasticity and has a modulus of elasticity that is higher than bone. It should be understood, however, that both of the first or primary friction area, layer or feature 24 and/or the second or secondary friction area, layer or feature 28 could comprise a relatively high modulus of elasticity or a modulus of elasticity that is higher than bone if desired.

Thus, at least one or both of the first or primary friction area, layer or feature 24 or the second or secondary friction area, layer or feature 28 may comprise a relatively high coefficient of friction with bone, while the underlying substrate or body 12 and the first or primary friction area, layer or feature 24 may comprise a relatively low modulus of elasticity and low coefficient of friction relative to bone. In the embodiment of FIGS. 1-5, the second or secondary friction area, layer or feature 28 comprises a higher coefficient of friction and higher modulus of elasticity compared to the first or primary friction area, layer or feature 24 and body 12 which facilitate the frictional engagement and locking of the orthopedic implant 10 in the patient, such as between the patient's vertebra.

Thus, it should be understood that while the body 12 and the first or primary friction area, layer or feature 24 and the second or secondary friction area, layer or feature 28 may be made from the same materials having the same coefficient of friction and modulus of elasticity, they could comprise different materials which have either the same or different coefficients of friction and/or the same or different moduli of elasticity. Also, the first or primary friction area, layer or feature 24 and the second or secondary friction area, layer or feature 28 could be different materials and their respective modulus of elasticity and coefficients of friction relative to bone may be different as mentioned earlier.

Again, it should be understood that one advantage of the embodiments being described is that they enhance the frictional engagement of the orthopedic implant 10 when it is implanted in the patient. Thus, the orthopedic implant 10 having the first or primary friction area, layer or feature 24 comprising the second or secondary friction area, layer or feature 28 will comprise a higher modulus of elasticity and higher coefficient of friction compared to bone.

Advantageously, the polymers or polymeric materials used in the past may be utilized in manufacturing the body 12 and the shortcomings of such materials can be used to provide the orthopedic implant 10 having the body 12 that has relatively high levels of lubricity, elasticity and smoothness, but which have been adapted, machined or processed as provided herein to provide relatively high modulus of elasticity and high coefficients of friction at the orthopedic implant 10-bone interface by providing the first or primary friction area, layer or feature 24 with the second or secondary friction area, layer or feature 28 as described herein.

As mentioned earlier, the first or primary friction area, layer or feature 24 may be machined, molded, integral extruded, sintered or deposited onto the body 12. The first or primary friction area, layer or feature 24 may be separate from or integral with the body 12 as mentioned earlier. Likewise, the second or secondary friction area, layer or feature 28 may be machined, molded, extruded, sintered or deposited directly on the first or primary friction area, layer or feature 24 and may also be separate from or integral with it. For example, the second or secondary friction area, layer or feature 28 may be sprayed onto, deposited on, melted to, or otherwise applied to or adhered to the first plurality of teeth or serrations 26 surfaces, such as surfaces 26a and 26b of each of the first plurality of teeth or serrations 26, and/or on each surface 12a1, 12a2, 12b1 and 12b2 having the first or primary friction area, layer or feature 24, thereby enhancing the frictional engagement between the orthopedic implant 10 and the bone. As mentioned earlier, the second or secondary friction area, layer or feature 28 may be deposited on these surfaces using a plasma vapor deposition process.

Figure 2:
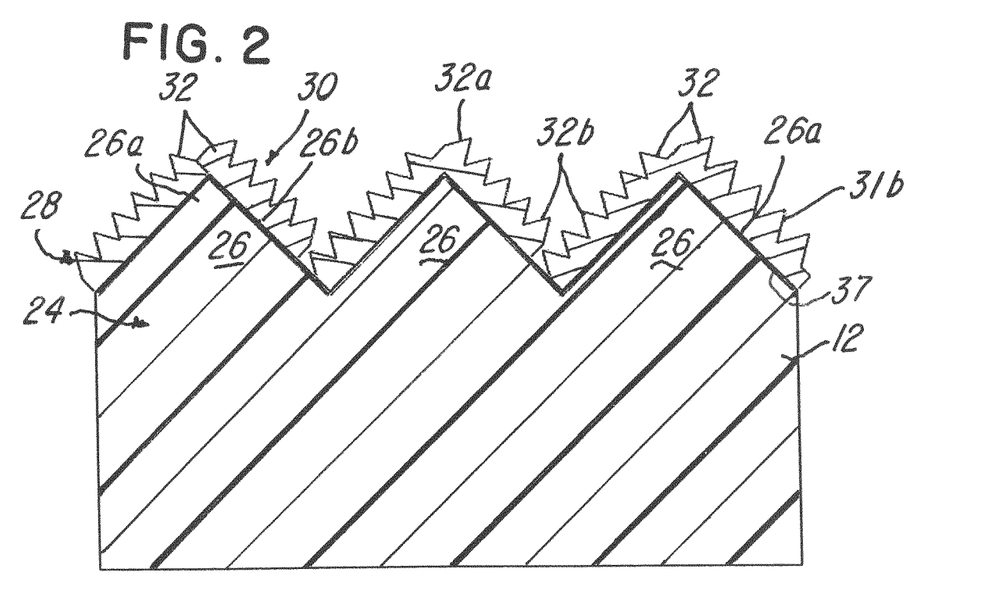
FIG. 2 is an enlarged view of a portion of the implant shown in FIG. 1 showing details of the primary friction feature and secondary friction feature.
Figure 3:
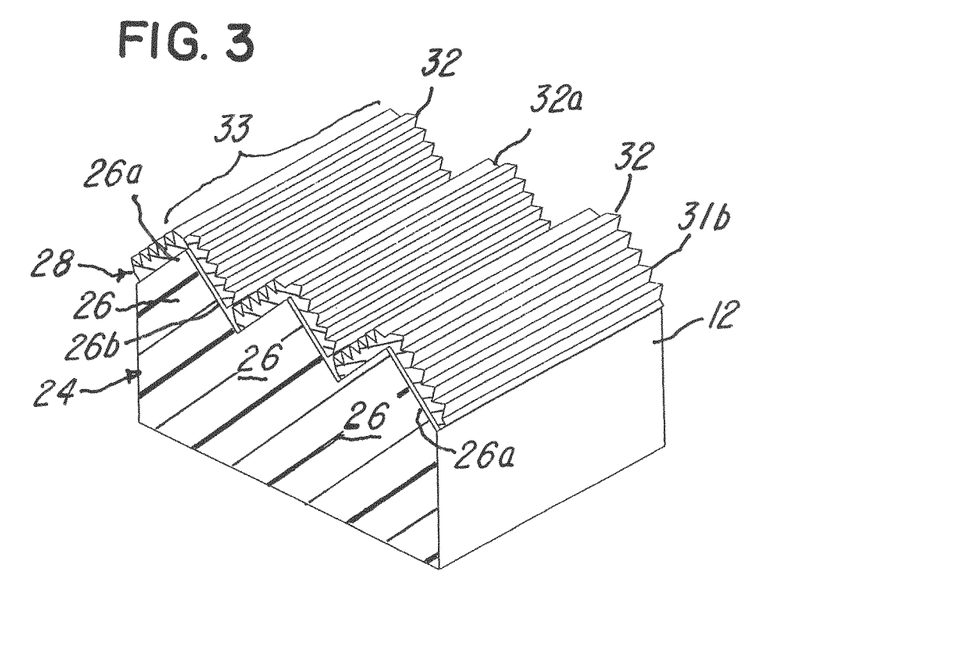
FIG. 3 is a perspective view of the enlargement shown in FIG. 2.

Returning to the embodiment of FIGS. 1-3, the first or primary friction area, layer or feature 24 comprises the first plurality of teeth or serrations 26 that have peaks and valleys in cross section and are elongated, with each tooth or serration being generally the same in shape and dimension. Likewise, the second or secondary friction area, layer or feature 28 is defined by the second plurality of teeth or serrations 32 that are machined into, integral with, adhered to or applied directly to the surfaces 26a and 26b of the first plurality of teeth or serrations 26 as illustrated in FIGS. 1-3. In the illustration being described, the plurality of teeth 32 are thermally bonded, adhered, impregnated, embedded on or in into the teeth 26. For ease of illustration, FIG. 2 shows bonding of the teeth or serrations 32 to teeth or serrations 26 with an adhesive 37, but it should be understood that the teeth may be adhered by other means. As with the first plurality of teeth or serrations 26, the second plurality of teeth or serrations 32, such as teeth 32a and 32b in FIG. 2, may each comprise generally the same shape and be elongated along the longitudinal axis and continuous as shown in FIG. 3. In other words, the first and second pluralities of teeth or serrations 26 and 32 may be regular in shape.

Note that the first plurality of teeth or serrations 26 are elongated and comprise surfaces 26a and 26b comprising the rows or strips 33 of the second plurality of teeth or serrations 32. The rows or strips 33 are made of metal or a metal alloy, such as titanium or other biocompatible substance capable of providing a high-friction layer, in the illustration and adhered to or overmolded with the body 12.

In the illustration, the orthopedic implant 10 is inserted into the patient and the first or primary friction area, layer or feature 24 and the second or secondary friction area, layer or feature 28 on surfaces 12a1, 12a2, 12b1 and 12b2 frictionally engage bone to secure the orthopedic implant 10 in the patient.

FIGS. 6-9B and 11-12B illustrate other embodiments with like parts being identified with the same part numbers except that one or more legends or prime marks ("'") have been added to distinguish the various embodiments of these figures.

Figure 11:
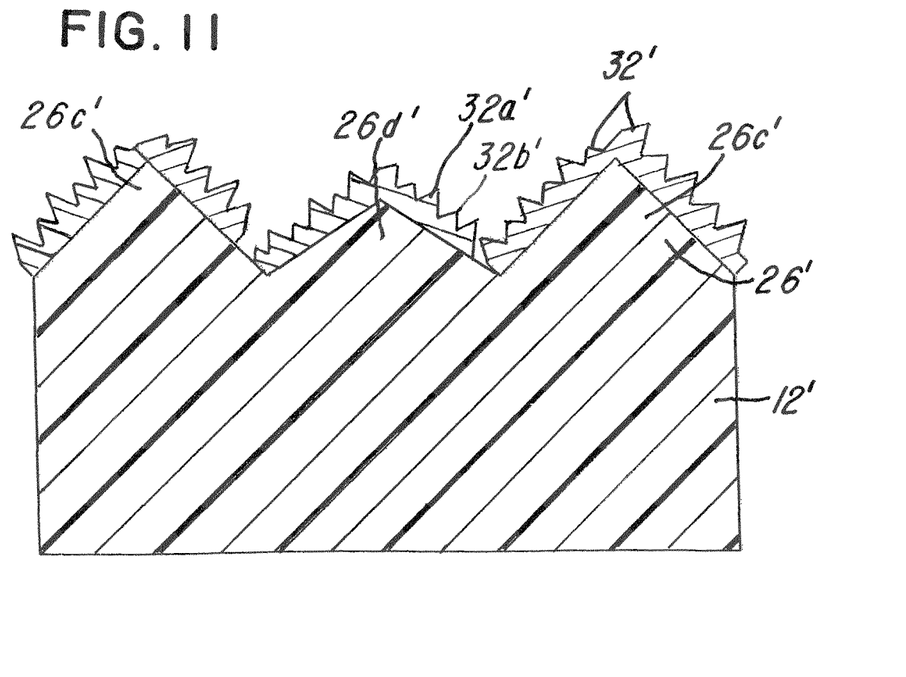

Note that the first plurality of teeth or serrations 26' in FIG. 11 comprises different cross-sectional shapes and sizes. Thus, the first and second pluralities of teeth or serrations 26' and 32' may be adapted to be irregular in shape, and the first plurality of teeth or serrations 26' in FIG. 11 could comprise different cross-sectional shapes and sizes. For example, note that tooth 26c' has a different shape and size compared to tooth 26d'.

Likewise, the shape or size of each individual tooth, such as teeth 32a' and 32b' (FIG. 11) of the second plurality of teeth or serrations 32' may be different. Thus, the individual teeth in each of the first and second plurality of teeth or serrations 26' and 32' could be the same or have different shapes, and they could have different pitches, depths, widths and the like and will be described later herein.

Figure 12A:
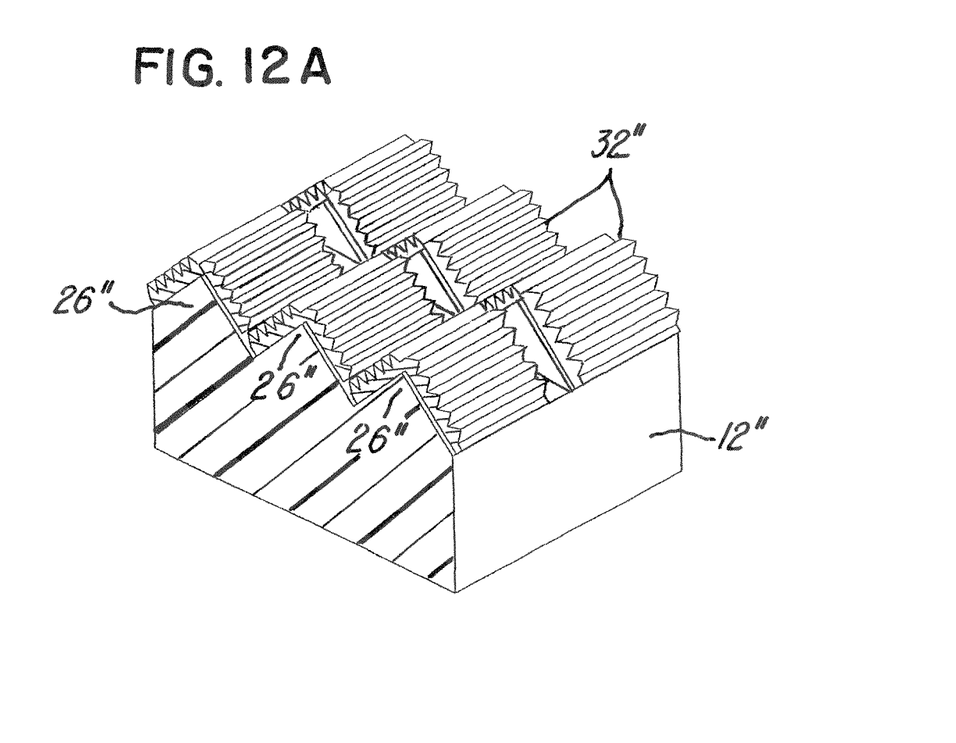
FIGS. 12A-12B illustrate embodiments wherein the primary friction feature or secondary friction feature are interrupted (FIG. 12A) along their longitudinal length and wherein the primary friction feature is not interrupted along its longitudinal length, but the secondary friction feature is interrupted (FIG. 12B).
Figure 12B:
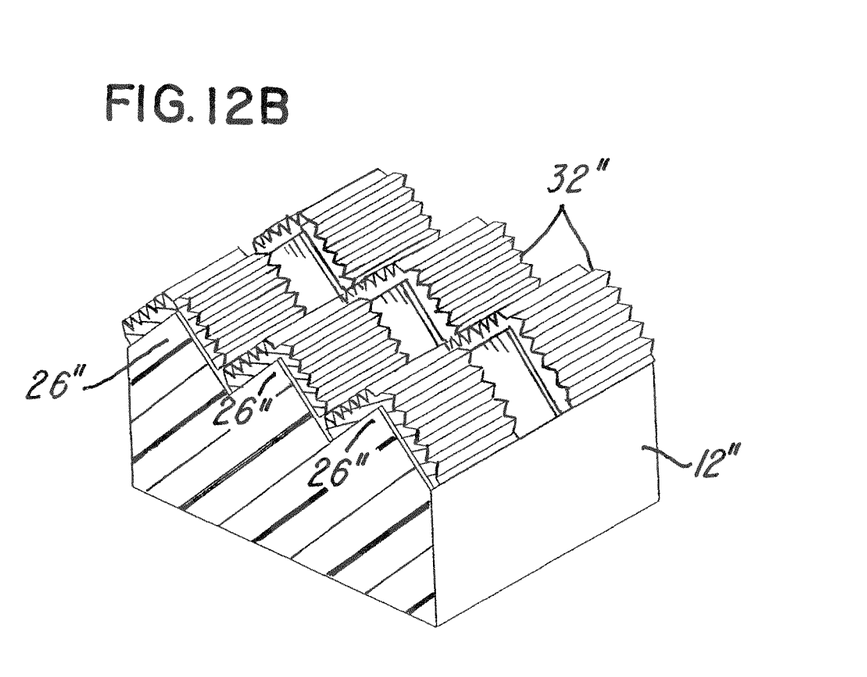

As mentioned, while the embodiment in FIGS. 1-3 illustrate that each of the first plurality of teeth or serrations 26 and the second plurality of teeth or serrations 32 are generally regular and uninterrupted as shown, but it should be understood that either at least one of both of the first and second pluralities of teeth or serrations 26 and 32 may be non-elongated and interrupted. For example, FIG. 12A illustrates that both the first plurality of teeth or serrations 26" and the second plurality of teeth or serrations 32" that are situated on or integral with each of the first plurality of teeth or serrations 26' are not continuous and are interrupted along their longitudinal axis. FIG. 12B illustrates an embodiment where only the second plurality of teeth or serrations 32" is interrupted, but not the first plurality of teeth or serrations 26". Alternatively, while the embodiments shown in FIGS. 12A and 12B illustrates first and second pluralities of teeth or serrations 26" and 32" being interrupted along their longitudinal axis, it should be understood that there may be a mixture of interrupted and uninterrupted teeth if desired.

Figure 6A:
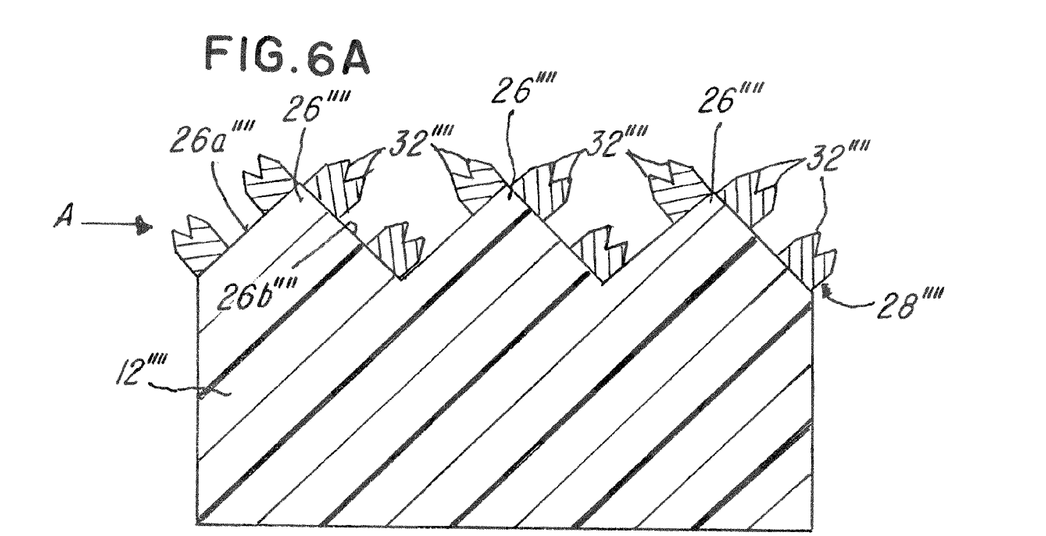
FIGS. 6A-6B is a view of another embodiment of the invention showing the elongated teeth that are interrupted or spaced in the direction of arrow A.
Figure 6B:
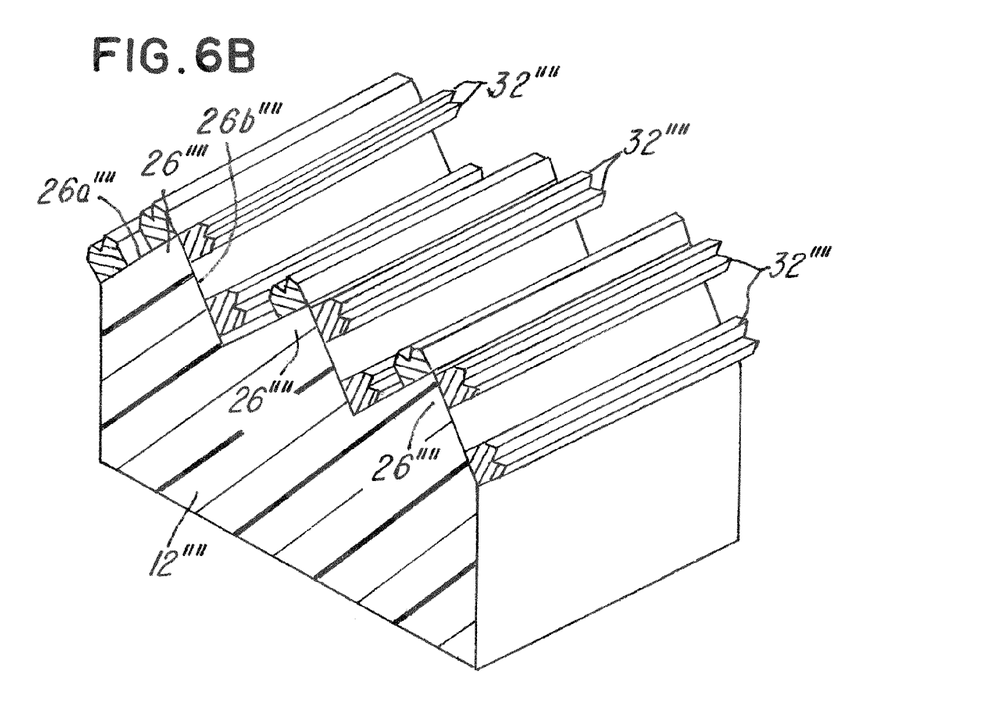

FIGS. 6A-6B illustrate still another embodiment wherein the second plurality of teeth or serrations 32"' are spaced or interrupted in the direction of arrow A in FIG. 6A-6B as shown. In this regard, it should be appreciated that one or both surfaces of each tooth, such as surfaces 26a"' and 26b"' in FIGS. 6A-6B, are shown as having at least one or a plurality of the second plurality of teeth or serrations 32"' mounted thereon or integral therewith. They are separately shown, but it should be understood that either one or both surfaces of the plurality of teeth or serrations 26"', such as surfaces 26a"' and 26b"', may either have or not have less teeth or one or more of the second plurality of teeth or serrations 32"'.

Figure 8A:
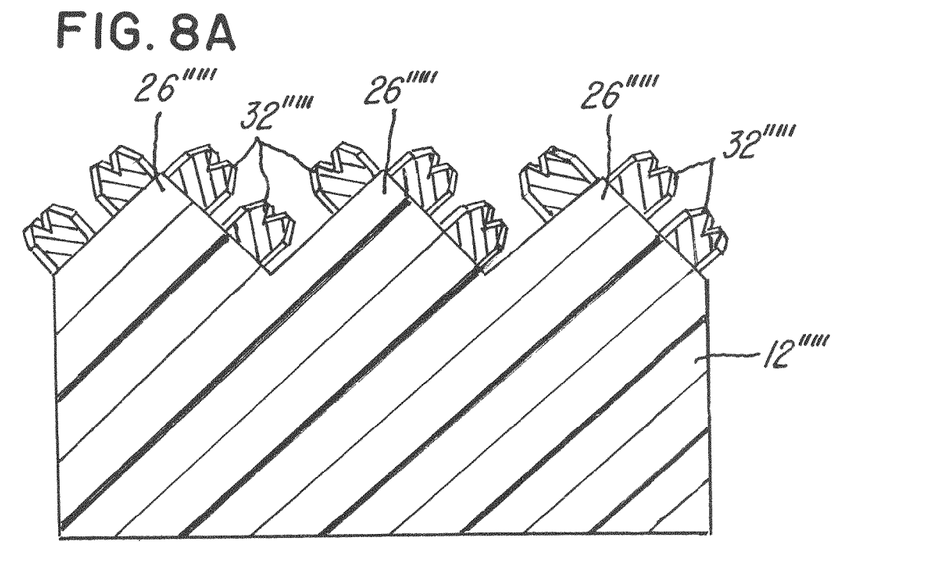
FIGS. 8A-8B are views of the secondary friction features having a curved or serpentine shape.
Figure 8B:
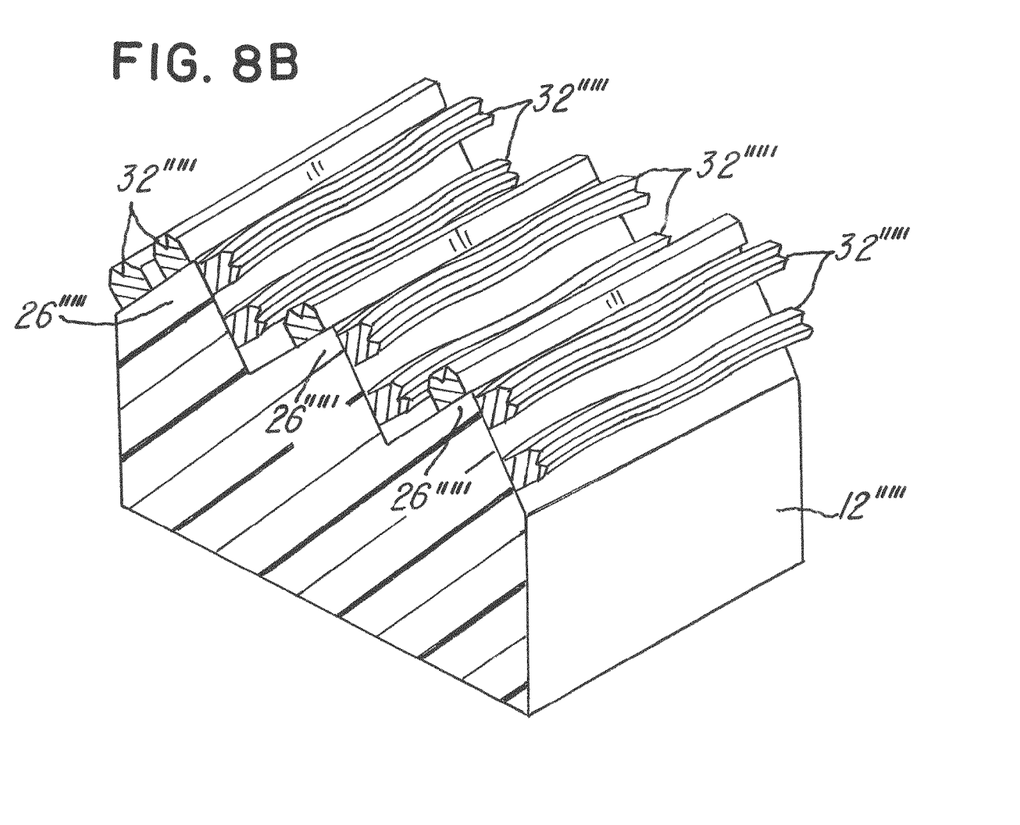
Figure 9A:
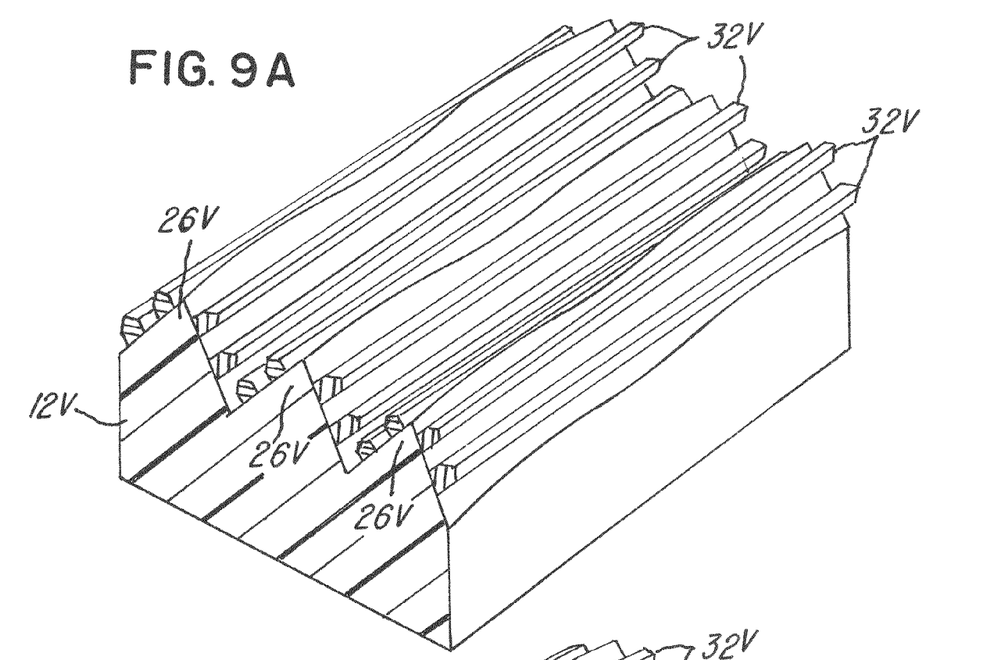
FIGS. 9A-9B illustrate an embodiment wherein the primary friction features have a curved or serpentine shape while the secondary friction features have a generally linear (FIG. 9A) shape or a curved (FIG. 9B) shape.
Figure 9B:
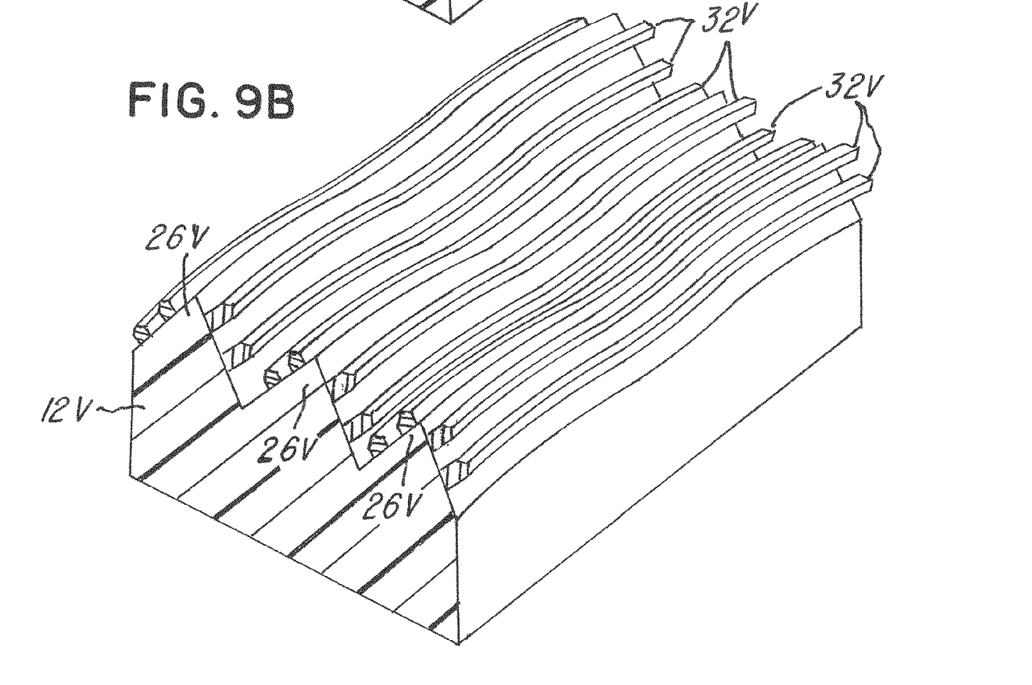

Still other embodiments are shown in FIGS. 8A-8B and 9A-9B wherein the second plurality of teeth or serrations 32"' are shown in a curved or serpentine and non-linear shape. It should be understood that the first plurality of teeth or serrations 26"' could also be provided in a serpentine or curved shape, with the second plurality of teeth or serrations 32"' as shown. Although not shown, the first plurality of teeth or serrations 26"' could be generally serpentine or curved (FIGS. 9A-9B) with the second plurality of teeth or serrations 32"' also having a serpentine or curved shape. FIGS. 8A-8B illustrate the first teeth or serrations 26 being generally linear with the second teeth or serrations 32 being curved or serpentine.

Although not shown, it should be appreciated that the embodiments shown in FIGS. 6, 7, 8A-8B, 9A-9B and 11 could be provided such that they are continuous and uninterrupted or discontinuous and interrupted. Likewise, the teeth illustrated in the figures could be provided such that the first and second pluralities of teeth or serrations 26 and 32 in the embodiments are not of the same cross-sectional dimension or shape. As mentioned earlier relative to FIG. 11, it should be understood that the individual tooth 26 and 32 could be adapted or provided so that they are neither regular nor symmetrical when viewed in one or more of the directions in arrow B, arrow C or arrow D in FIGS. 1-1A. Thus, individual teeth of both the first plurality of teeth or serrations 26 and the second plurality of teeth or serrations 32 could have different pitches, depths, widths and the like.

Referring now to the embodiment shown in FIGS. 4, 5, 10A and 10B, the second or secondary area, layer or feature 28 may be provided in the form of a deposit or coating 40. As with prior embodiments, those parts that are the same or similar to the parts shown in FIGS. 1-1A are identified with the same part number except that prime marks ("'''") has been added to the part numbers in FIGS. 4 and 5 and a mark ("VI") has been added to those parts in the embodiment of FIGS. 10A and 10B. As mentioned earlier, the second or secondary friction area, layer or feature 28" coating or deposit 40" could be deposited onto, sprayed onto, melted onto or otherwise applied to the first or primary area, layer or feature 24". In the illustration being described relative to FIGS. 4 and 5, the coating 40" comprises a plurality of particles 42" that are deposited onto, adhered to or otherwise applied to surfaces 12a1", 12a2", 12b1" and 12b2". In this embodiment, the coating 40" is applied using a plasma layer deposition In this regard, the body 12" defines the orthopedic implant 10" for implanting into the patient. The first or primary area, layer or feature 24" in this embodiment is similar to the embodiment in FIGS. 1-1A in that each surface 12a1", 12a2", 12b1" and 12b2" has or defines a plurality of teeth or serrations 26". In the illustration being described, each of the plurality of teeth or serrations 26" comprises a first surface 26e" (FIG. 4) and the second surface 26f" as shown having the coating or deposit 40" of particles 42". Note also that areas or surfaces 12a3", 12a4", 12b3" and 12b4" (FIG. 5) also have the coating or deposit 40" of particles 42. In the illustration being described, the coating or deposit 40" is titanium, cobalt or associated alloys. As previously mentioned, the teeth or serrations 26 may be asymmetrical to enhance frictional engagement.

Figure 10A:
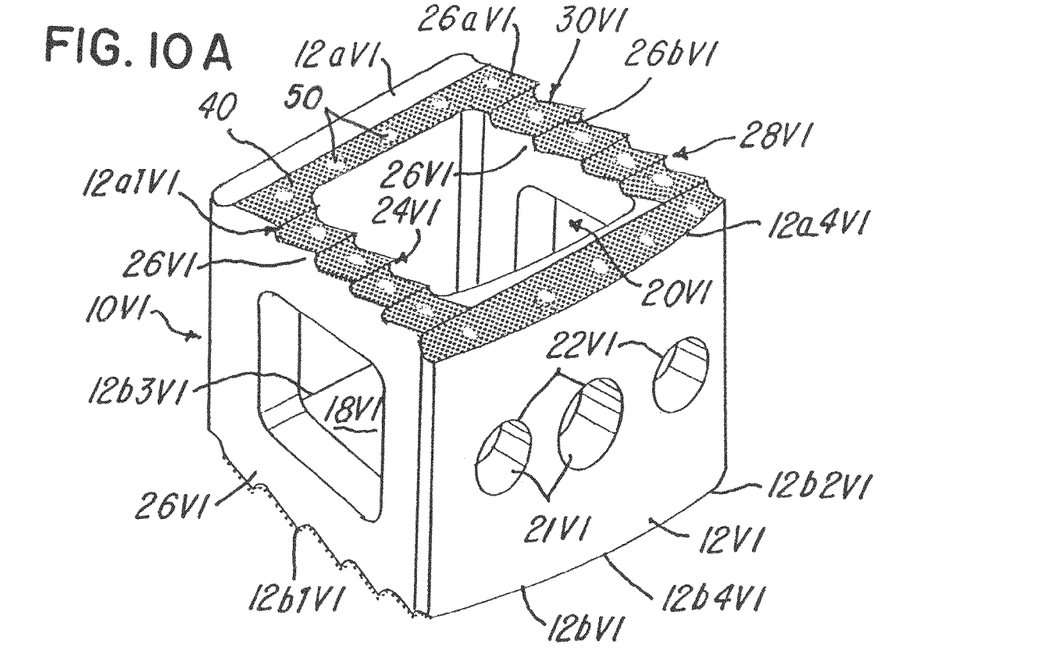
FIGS. 10A-10B illustrate another embodiment similar to FIGS. 4 and 5 wherein the deposit or coating is selectively placed.
Figure 10B:
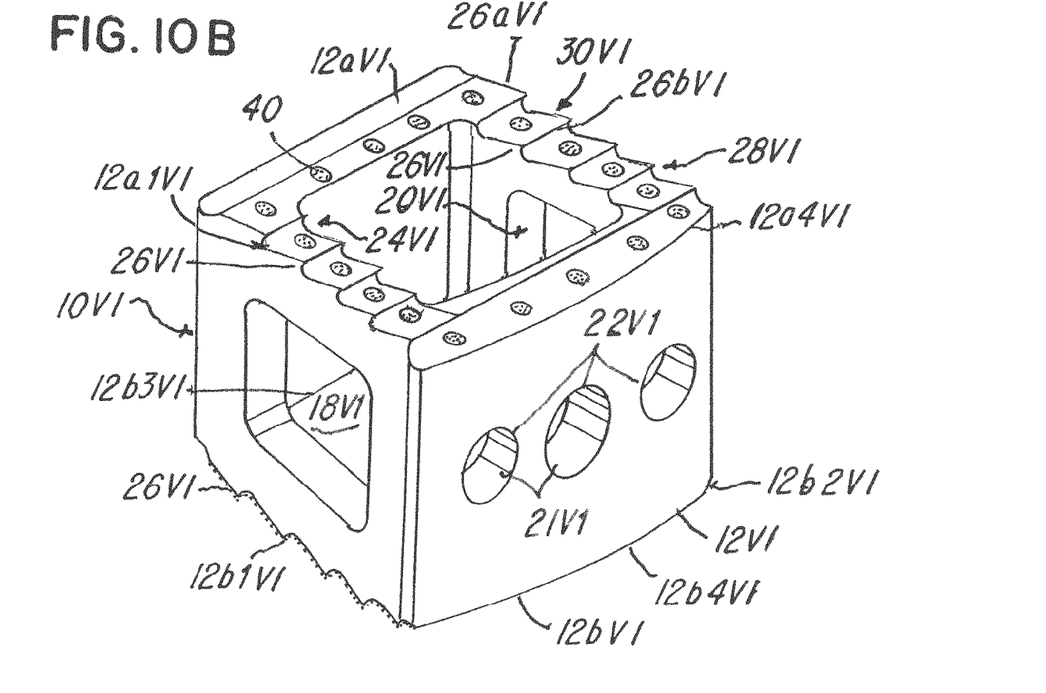

Thus, each of the ends 12a" and 12b" in the illustration being described comprise the coating or deposit 40" of particles 42". In the illustration shown in FIGS. 4 and 5, note that the layer or coating 46" is continuous over the first or primary area, layer or feature 24" and on ends 12a" and 12b", but it should be understood that the ends 12a'" and 12b'" could be spot coated, and less than the entire first or primary area, layer or feature 24" may have no deposit or coating thereon. This is illustrated in FIGS. 10A-10B where some of the areas of the first teeth or serrations 26, such as the areas 50, may not comprise the deposit or coating as shown. Stated another way, the coating $40^{VI}$ or deposit 40" may be selectively provided or applied to those surfaces of the orthopedic implant 10" that engage bone.

Figure 4:
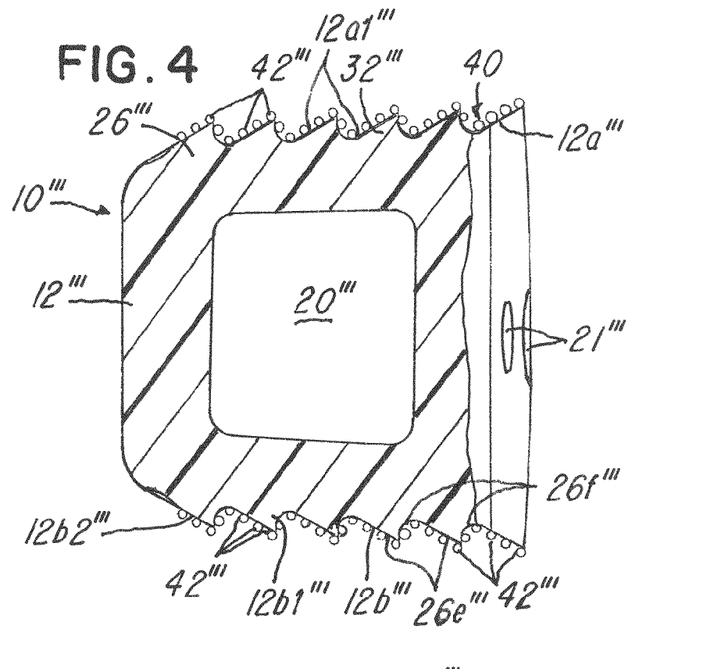
FIG. 4 is a sectional view taken along the line 4-4 in FIG. 5 illustrating the secondary friction feature in the form of a deposit or coating on the primary friction feature.
Figure 5:
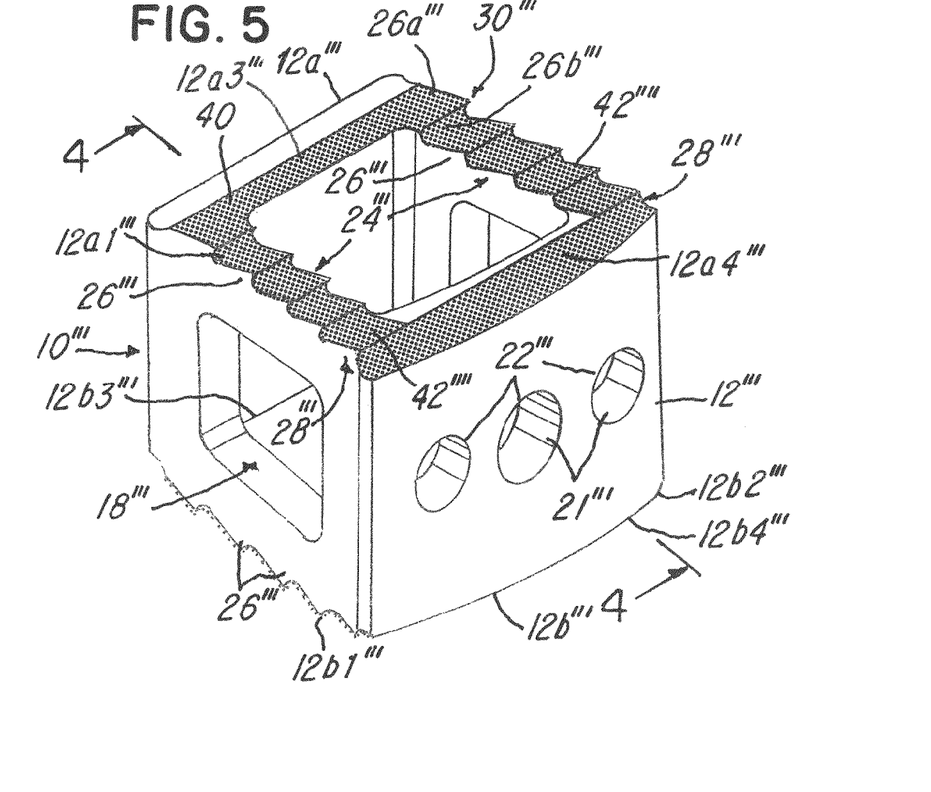
FIG. 5 is a view of another embodiment showing the primary friction feature as teeth and the secondary friction feature as a deposit or coating.
Figure 7:
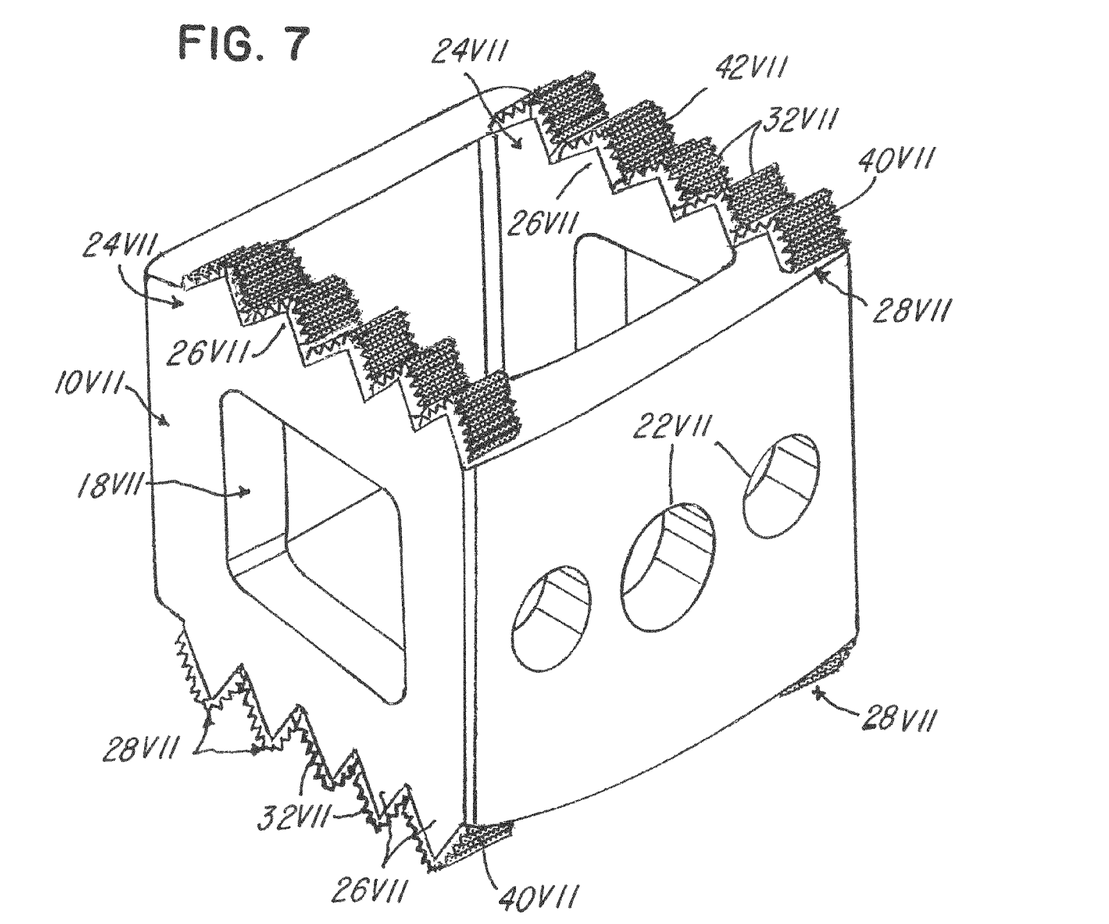
FIG. 7 is a view of another embodiment of the invention similar to FIG. 5.

In the embodiment of FIG. 7, the surfaces, such as surfaces $32b^{VII}$ and $32c^{VII}$ of each of the second plurality of teeth or serrations $32^{VII}$ comprises a deposit or coating or deposit $40^{VII}$ of particles $42^{VII}$ similar to that shown in FIG. 5. Thus, it should be understood that the embodiment shown in FIGS. 4 and 5 illustrates the second or secondary area, layer or feature 28'" comprising the deposit or coating as shown, whereas the embodiment illustrated in FIG. 7 shows the first or primary area, layer or feature $24^{VII}$ having the first plurality of teeth or serrations $26^{VII}$ having the second or secondary area, layer or feature $28^{VII}$ in the form of the second plurality of teeth or serrations $32^{VII}$ which themselves have the coating or deposit $40^{VII}$ of particles $42^{VII}$.

In the illustrations being described, any particles $42^{VII}$ that are applied, sprayed, adhered, coated, deposited or melted onto at least one of the first or primary area, layer or feature $24^{VII}$ or the second or secondary area, layer or feature $28^{VII}$ may be round, not round or circular or non-circular, coarse, acyclic, and may form a continuous layer or discontinuous or discreet layer on all or only a portion of the first or primary area, layer or feature $24^{VII}$ or the second or secondary area, layer or feature $28^{VII}$. As mentioned earlier, the first or primary area, layer or feature $24^{VII}$ and the second or secondary area, layer or feature $28^{VII}$ may be comprised of the same substance or material or they could comprise different materials, such as a metallic or metallic alloy as mentioned earlier herein, or a thermal plastic such as PEEK. In the illustration of FIGS. 4, 5, 7 and 10A-10B, the layer or coating 46" is a metallic coating of titanium, cobalt or associated alloys deposited on the first plurality of teeth or serrations 26" using plasma vapor deposition.

Advantageously, the second or secondary area, layer or feature in all embodiments augments at least a portion or all of the external first or primary area, layer or feature, such as the surfaces 26a, 26b of the one or more of the first plurality of teeth or serrations 26 in the embodiment of FIGS. 1-3 in order to enhance or add high friction to the engagement surfaces of the orthopedic implant 10. While traditional implants have engagement surfaces that engage bone, the embodiments described herein improve the frictional engagement between the bone and the orthopedic implant 10 by adding the second or secondary area, layer or feature 28 which provides improved frictional engagement between the frictional surfaces of the orthopedic implant 10 and bone.

Advantageously, one advantage of the orthopedic implant 10 as described herein is that it improves the inherently low levels of bone-orthopedic implant 10 interface and surface interaction. The primary frictional features described herein add a surface material, such as a metallic surface material, to the first or primary friction area, layer or feature 24 which provides low lubricity, low elasticity and the secondary frictional features defined by the second or secondary friction area, layer or feature 28. The embodiments described provide or comprise a design that will maintain the biomechanical properties of the orthopedic implant 10 while addressing frictional shortcomings of the orthopedic implant 10 and the interfaces between the bone and the implants of the past.

While the system, apparatus and method herein described constitute preferred embodiments of this invention, it is to be understood that the invention is not limited to this precise system, apparatus and method, and that changes may be made therein without departing from the scope of the invention which is defined in the appended claims.

What is claimed is:

1. An orthopedic implant comprising:
a substrate material adapted to provide the orthopedic implant;
a primary friction area located on or integral with said substrate material, said primary friction area having a primary surface having a primary frictional feature; and
a secondary friction area located on or integral with said primary surface and defining a secondary frictional feature;
said primary friction area and said secondary friction area defining a friction interface zone, said secondary friction area increasing a friction of said primary surface to enhance a frictional engagement between said primary surface and at least one bone;
wherein said primary frictional feature defines a plurality of primary teeth;
wherein said secondary frictional feature defines a plurality of secondary teeth on or integral with said primary friction area;
wherein at least one of said plurality of primary teeth has at least one surface that does not have said secondary frictional feature;
wherein said primary friction area and said secondary friction area are at least one of machined, molded, extruded or sintered substrate.

2. The orthopedic implant as recited in claim 1 wherein said substrate material is a polymeric substrate.

3. The orthopedic implant as recited in claim 1 wherein said secondary friction area comprises at least one of a microscopically or macroscopically rough surface.

4. The orthopedic implant as recited in claim 1 wherein said secondary friction area is regular in shape.

5. The orthopedic implant as recited in claim 1 wherein said secondary friction area is irregular in shape.

6. The orthopedic implant as recited in claim 1 wherein said substrate material is made from a thermoplastic.

7. The orthopedic implant as recited in claim 6 wherein said thermoplastic is a polyetheretherketone (PEEK).

8. The orthopedic implant as recited in claim 1 wherein a modulus of elasticity of said substrate material is less than or equivalent to bone.

9. The orthopedic implant as recited in claim 8 wherein said substrate material has a low coefficient of friction with bone.

10. The orthopedic implant as recited in claim 8 wherein at least one of said primary friction area or said secondary friction area has a modulus of elasticity that the same as or greater than bone.

11. The orthopedic implant as recited in claim 1 wherein at least one of said primary friction area or said secondary friction area being made from a metal or metallic alloy.

12. The orthopedic implant as recited in claim 1 wherein at least one of said primary friction area or said secondary friction area having a modulus of elasticity that is the same as or greater than bone.

13. The orthopedic implant as recited in claim 1 wherein at least one of said primary friction area or said secondary friction area comprising a higher coefficient of friction with bone.

14. The orthopedic implant as recited in claim 13 wherein at least one of said primary friction area or said secondary friction area has a modulus of elasticity that is the same as or greater than bone.

15. The orthopedic implant as recited in claim 1 wherein said primary friction area comprising a higher coefficient of friction with bone and said secondary friction area comprising a higher coefficient of friction than said primary friction area.

16. The orthopedic implant as recited in claim 1 wherein said primary friction area having a modulus of elasticity that is the same as or greater than bone and said secondary friction area having a modulus of elasticity that is the same or greater than said primary friction area.

17. The orthopedic implant as recited in claim 1 wherein said secondary frictional feature is integral with or welded to said primary frictional feature.

18. The orthopedic implant as recited in claim 1 wherein said plurality of secondary teeth comprise points or peaks on or integral with said plurality of primary teeth.

19. The orthopedic implant as recited in claim 18 wherein said plurality of primary teeth are neither regular nor symmetrical.

20. The orthopedic implant as recited in claim 18 wherein said plurality of primary teeth are regular and symmetrical.

21. The orthopedic implant as recited in claim 1 wherein said primary frictional feature and said secondary frictional feature are made from different materials.

22. The orthopedic implant as recited in claim 1 wherein said primary frictional feature and said secondary frictional feature are made from the same materials.

23. The orthopedic implant as recited in claim 1 wherein at least one of said primary frictional feature, said secondary frictional feature or said substrate material is made from a different material than the others.

24. The orthopedic implant as recited in claim 1 wherein said secondary frictional feature increases a coefficient of friction of said orthopedic implant and bone.

25. The orthopedic implant as recited in claim 1 wherein said orthopedic implant is a spinal implant.

26. The orthopedic implant as recited in claim 25 wherein said spinal implant is a cage.

27. An orthopedic implant comprising:
a body comprising a composite material;
a first friction area situated between the body and bone of a patient when the orthopedic implant is implanted in the patient, said first friction area comprising a plurality of primary teeth having generally the same shape; and
a second friction area associated with said first friction area for directly engaging said bone;
wherein said second friction area defines a plurality of secondary teeth on or integral with said first friction area, at least one of said plurality of primary teeth has a surface that is not co-planar with said first friction area and that does not have said second friction area thereon;
each of said first and second friction areas for improving a frictional engagement between said bone and said orthopedic implant;
wherein said first friction area and said second friction area are at least one of machined, molded, extruded or sintered.

28. The orthopedic implant as recited in claim 27 wherein said body and said first friction area each have a modulus of elasticity that is lower than a modulus of elasticity of said second friction area.

29. The orthopedic implant as recited in claim 27 wherein said second friction area defines a frictional engaging surface that increases a coefficient of friction between said first friction area and said bone.

30. The orthopedic implant as recited in claim 27 wherein said body is made from a polymeric material, and at least one of said first or second friction areas comprises a metallic or metallic alloy.

31. The orthopedic implant as recited in claim 27 wherein said plurality of secondary teeth of said second friction area is uninterrupted.

32. The orthopedic implant as recited in claim 27 wherein said composite material is made from a thermoplastic.

33. The orthopedic implant as recited in claim 27 wherein said thermoplastic is a polyetheretherketone (PEEK).

34. The orthopedic implant as recited in claim 27 wherein a modulus of elasticity of said composite material is less than or equivalent to bone.

35. The orthopedic implant as recited in claim 34 wherein a coefficient of friction associated with said composite material and bone is lower than a coefficient of friction between said second friction area and said bone.

36. The orthopedic implant as recited in claim 34 wherein each of said first friction area and said second friction area comprise a higher coefficient of friction with bone.

37. The orthopedic implant as recited in claim 27 wherein each of said first friction area and said second friction area are made from a metal or metallic alloy and said body is made of a polymer.

38. The orthopedic implant as recited in claim 27 wherein each of said first friction area or said second friction area have a modulus of elasticity that is the same as or greater than bone.

39. The orthopedic implant as recited in claim 27 wherein said second friction area is integral with, welded to, adhered to said first friction area.

40. The orthopedic implant as recited in claim 27 wherein said plurality of secondary teeth of said second friction area define a plurality of points or peaks on said first friction area.

41. The orthopedic implant as recited in claim 40 wherein said plurality of points or peaks are neither regular nor symmetrical.

42. The orthopedic implant as recited in claim 40 wherein said plurality of points or peaks are regular and symmetrical.

43. The orthopedic implant as recited in claim 27 wherein said orthopedic implant is a spinal implant.

44. The orthopedic implant as recited in claim 43 wherein said spinal implant is a cage.

* * * * *